United States Patent
Pohl et al.

(10) Patent No.: US 10,352,863 B1
(45) Date of Patent: Jul. 16, 2019

(54) METHOD FOR OPTIMIZING DETECTION OF INELASTICALLY SCATTERED LIGHT FROM A DISTANT TARGET BY MEASURING THE TARGET DISTANCE USING INELASTICALLY SCATTERED LIGHT

(71) Applicant: Alakai Defense Systems, Inc., Largo, FL (US)

(72) Inventors: Kenneth R. Pohl, Clearwater, FL (US); Christopher Neglia, Largo, FL (US)

(73) Assignee: Alakai Defense Systems, Inc., Largo, FL (US)

( * ) Notice: Subject to any disclaimer, the term of this patent is extended or adjusted under 35 U.S.C. 154(b) by 15 days.

(21) Appl. No.: 15/820,039

(22) Filed: Nov. 21, 2017

Related U.S. Application Data

(60) Provisional application No. 62/425,652, filed on Nov. 23, 2016.

(51) Int. Cl.
  *G01N 21/65* (2006.01)

(52) U.S. Cl.
  CPC ....... *G01N 21/65* (2013.01); *G01N 2201/061* (2013.01); *G01N 2201/064* (2013.01)

(58) Field of Classification Search
  CPC ............ G01N 21/65; G01N 2201/061; G01N 2201/064
  See application file for complete search history.

(56) References Cited

U.S. PATENT DOCUMENTS

| | | | |
|---|---|---|---|
| 4,518,256 A | 5/1985 | Schwartz | |
| 4,634,272 A | 1/1987 | Endo | |
| 6,466,307 B2 | 10/2002 | Chien et al. | |
| 8,072,595 B1 | 12/2011 | Bastiaans et al. | |
| 8,125,627 B2 | 2/2012 | Dottery et al. | |
| 8,724,097 B2 | 5/2014 | Pohl et al. | |
| 9,157,801 B2 | 10/2015 | Dottery et al. | |
| 2007/0222981 A1* | 9/2007 | Ponsardin | G01J 3/02 356/301 |
| 2008/0198365 A1 | 8/2008 | Treado et al. | |
| 2010/0266491 A1* | 10/2010 | Farokhzad | A61K 9/5153 424/1.29 |
| 2010/0309464 A1 | 12/2010 | Treado et al. | |
| 2015/0013035 A1* | 1/2015 | Humphris | G01Q 20/02 850/1 |
| 2018/0053799 A1* | 2/2018 | Otani | G01C 3/06 |

* cited by examiner

*Primary Examiner* — Hina F Ayub
(74) *Attorney, Agent, or Firm* — McKee, Voorhees & Sease, PLC

(57) ABSTRACT

The present invention comprises a novel approach for optimizing detection performance of a standoff optical detection system using the inelastic scattering of light from the target and/or inelastic scattering of light from molecules between the light emitting source and the target. This is a useful approach primarily for systems which already employ a pulsed light source, a detector, and a timing mechanism but whose primary function is not the detection of range. Using this methodology removes the need to deploy a secondary device to find range or augments the ability of any included range finder to widen the overall system operating envelope, reliability, and performance.

13 Claims, 11 Drawing Sheets

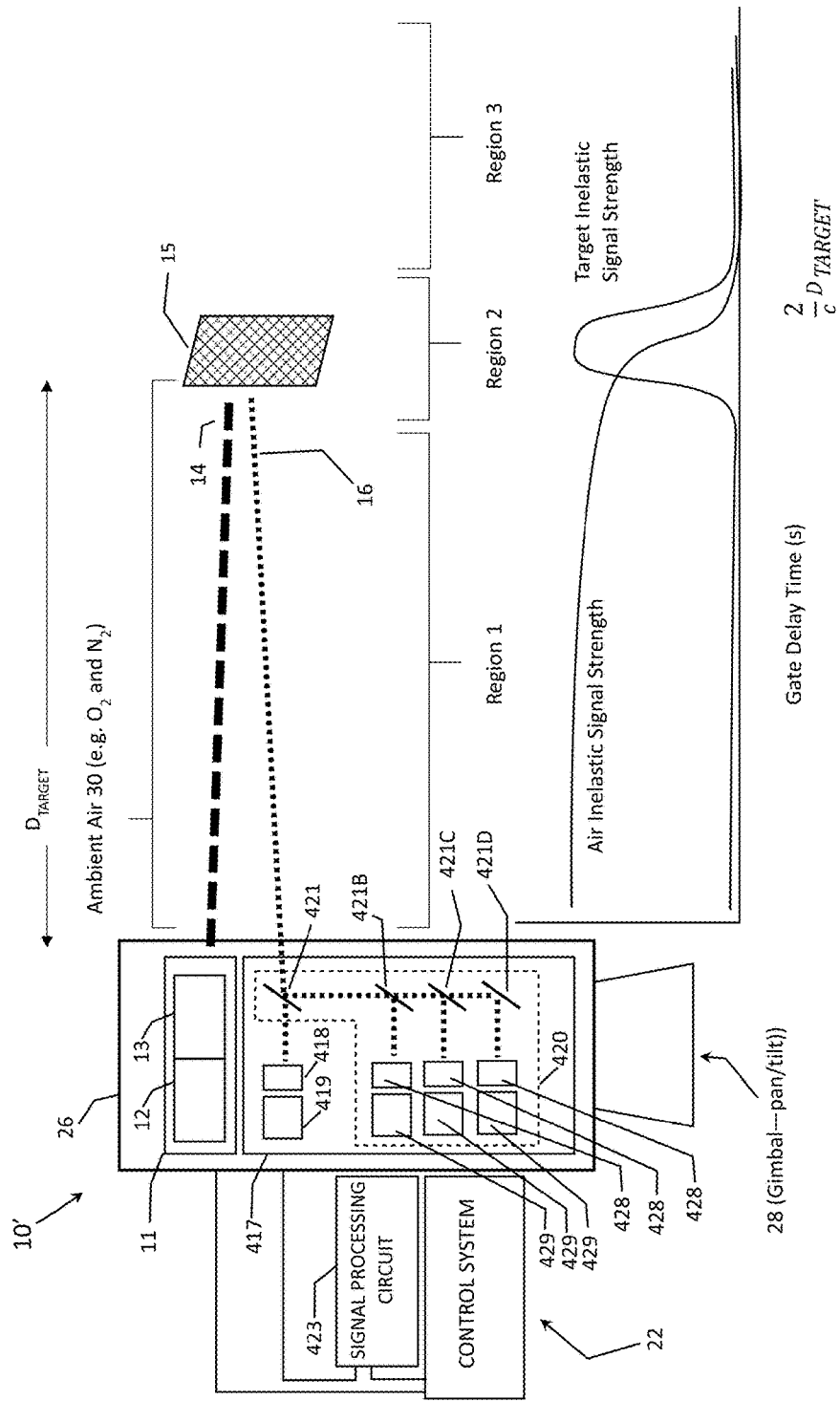
FIGURE 8 (Alternate Embodiment)

METHOD FOR OPTIMIZING DETECTION OF INELASTICALLY SCATTERED LIGHT FROM A DISTANT TARGET BY MEASURING THE TARGET DISTANCE USING INELASTICALLY SCATTERED LIGHT

CROSS-REFERENCE TO RELATED APPLICATIONS

This application claims the benefit of Provisional Application U.S. Ser. No. 62/425,652 filed on Nov. 23, 2016, all of which is herein incorporated by reference in its entirety.

GOVERNMENT RIGHTS CLAUSE

This invention was made with Government support under contract no. W911NF-14-C-0156 issued by the U.S. Army. The Government has certain rights in the invention.

1 BACKGROUND OF THE INVENTION

1.1 Field of the Invention

The present invention is a methodology for optimizing performance of a standoff optical spectroscopy system using measurements of optical inelastic scattering from an intermediate medium between the sensor and target and/or utilizing optical inelastic scattering from the target.

1.2 Related Art

Optical range-finding or LIDAR (light detection and ranging) is a well-known method for measuring distance. An LIDAR range-finder works by emitting pulses of light (typically infrared but visible or ultraviolet are also possible) towards the target and detecting reflected light from the target. The round-trip travel time of the light to the target and back can be measured and the distance calculated from that time. For instance, Endo (U.S. Pat. No. 4,634,272 A) and Schwartz (U.S. Pat. No. 4,518,256 A) teach methods of using an optical transmitter and array of optical sensors to detect multiple objects and measure their distance and direction. One weakness of LIDAR range-finding and object detection is that it requires the target to be retro-reflective, i.e. some portion of the light must elastically scatter (reflect) off the target back to the rangefinder. Targets with anti-reflective coatings, absorptive coatings, or even transparent targets can degrade the detection performance by reducing the elastic scattered signal. Another weakness of LIDAR is that measuring target range through an intermediate medium that is partially reflective, such as smoke or fog, significantly complicates the measurement, because these materials retro-reflect a portion of the light back to the receiver, generating signals at times earlier than the signal from the target. Another weakness of LIDAR is that it can be jammed by a target or nearby object emitting pulsed light at the same wavelength.

Standoff optical spectroscopy (SOS), such as standoff spontaneous Raman spectroscopy or standoff diffuse reflectance spectroscopy, is a useful technique for analyzing material composition in situations where contact with the analyte is either not desirable or not feasible. SOS is typically performed by projecting light from an ultraviolet, visible, or infrared source, such as a laser, onto a target of interest which is some distance away, and collecting the scattered light onto a detection system which can measure the scattered light intensity at one or more wavelengths or ranges of wavelengths.

One common detection system for standoff optical spectroscopy utilizes spontaneous Raman scattering. A common standoff Raman spectroscopy system comprises at least one monochromatic optical source, typically a laser, a transmit subsystem to direct light from the source towards a target, a receive subsystem comprising optical elements to gather/collect light from the target, optical elements to filter out undesired wavelengths, a device for selecting a wavelength to impinge on a detector or a device to disperse light of a range of wavelengths onto elements of a detector, a detector for measuring the intensity of the selected wavelength(s) of light, a control subsystem for coordinating the actions of the light source, detector and wavelength-selective elements, an analysis subsystem which records and processes signals from the detector and any ancillary sensors (such as sensor and air temperature, atmospheric pressure, laser power, or other factors which may influence the measured spectrum), and other mechanical, electrical, computer, communication, and user interface subsystems as needed. The foregoing combination of components and their operation to interrogate targets at stand-off distances with excitation energy and detect presence of chemical species of interest by evaluation of inelastic scattering from the target with Raman spectroscopy, is well-known to those of skill in this technical field. A few examples, commonly-owned by the owner of the present invention, are: U.S. Pat. No. 8,125,627 to inventors Dottery, et al.; U.S. Pat. No. 8,724,097 to inventors Pohl et al.; and U.S. Pat. No. 9,157,801 to inventors Dottery, et al.; each of which is incorporated by reference herein. Other configurations are well known. The transmit subsystem and the receive subsystem may be integrated into a single assembly (in which case the entire assembly is typically referred to as the detection system) or may be separated.

Since the relative intensity of Raman-scattered light at various wavelengths depends on the chemical makeup of the material scattering the light, chemical analysis of the target is accomplished by analyzing the wavelength spectrum of the returned light. For standoff Raman spectroscopy, it is often desirable to separate the Raman spectrum from light scattered by the target to be analyzed from the Raman spectrum generated by interactions with other objects or materials (herein called "background"). Common causes of background include Raman scattering from an intermediate medium such as air between the detection system and the target, intermediate material such as dust or objects that partially occlude the target, material beyond the target if the target does not completely occlude the emitted light, and material not in the intended light path which generates signal due to multiple scattering events.

A method for separating the desired spectrum from the background spectrum in standoff Raman spectroscopy as taught by Dottery U.S. Pat. No. 9,157,801 is to utilize a pulsed emission source with a short duration (typically less than 100 nanoseconds) and a detection system which can separate, measure, or select signals based on received time. This is closely related to the concept of light detection and ranging (LIDAR) in which ranges are calculated using the delay between emission and detection time, although LIDAR systems typically utilize detection of reflected light rather than inelastic scattered light. Reflected light (elastically scattered light) is light scattered without a meaningful change in wavelength. As is well-known in the art and expressed in published patent application US 08/0198365 A1 to inventors Treado, et al. which is incorporated by reference herein, Raman scattering spectra is "inherently richer" in molecular-specific "fingerprint signatures" and therefore can be a valuable tool for molecular identification of materials. This is particularly true of many explosive materials, because they have strong, unique Raman spectra that are essentially "fingerprints" of the vibrational spectrum of such molecules.

Such non-destructive, contactless, stand-off interrogation of materials has highly significant potential. One context is remote detection of explosives or otherwise hazardous materials. It can literally be a life-saving tool. However, the challenges for accurate, timely, and practical techniques are many. One is spatial. Sufficient stand-off interrogation distances (sometimes tens if not hundreds of meters) make it difficult to ensure and know if the excitation energy is optimally interrogating the target and if the light energy collected thereafter is optimally from the target and not from other materials (including the molecules that make up ambient air between detector and target). Another is temporal. Can the technique obtain and process sufficient information in a short-enough time to be practical? Although interrogation and return scattering are essentially at the speed of light, the ability to coordinate, collect and process complex content is in the microsecond, nanosecond, and even shorter time scales. This adds a level of complexity and unpredictability. Another is signal-to-noise ratio. Raman content is notoriously weak relative to other content in light collected from the target, so it is difficult to extract. Another is accuracy and precision. The difficulties in translating spectra from scattering from an unknown material into identification of molecules is well-known.

The quality with which the desired Raman signal can be separated from the background Raman signals is largely determined by a combination of factors including (1) the duration of the emission pulse, (2) the accuracy and precision with which the received signal time can measured or selected, (3) the accuracy and precision of the known distance to the desired target, and (4) the accurate quantification of any timing delays within the system.

The duration of the emission pulse affects the separation of background signals from target signals because the received spectrum at any given time is a summation of emissions generated over a range of distances which is directly proportional to the pulse duration. For a pulse duration of $\Delta T$, the received signal at time T after the beginning of the emission pulse is a summation of signals generated at ranges of $$\frac{c}{2}(T - \Delta T) \text{ to } \frac{c}{2}T$$

where c is the speed of light. Therefore, a short pulse duration is desirable, since this will mix less signal from background materials in front of or behind the target with signals from the target. Timing accuracy and precision controls a similar mixing of background and signal, because to ensure all the signal from the target is collected, the signal collection duration must be larger than any timing errors.

In one standoff Raman implementation, the receive system incorporates an electro-optical gate component or capability, such as an intensifier tube, photomultiplier tube, Kerr gate, or other. These types of gates are well-known in to those skilled in the art, including how to implement them. Signal light is allowed through the gate for a set period of time (starting at a time $T_{delay}$ after pulsed emission from the source width until a later time $T_{delay}+T_{gate}$), with $T_{delay}$ typically selected based on target distance as measured or estimated using some means such as a rangefinder. In another implementation, the receive system incorporates a detector and signal processing system which are able to accurately measure signal intensities and variations at rates sufficient to select the signal at a particular time of interest. In this case, the receive system typically requires a bandwidth in excess of 10 MHz (and sometimes in excess of 100 MHz). Again, it is common practice to use a measured or estimated target distance to predetermine which portions of the processed signal are largely due to desired signal.

A few examples, all incorporated by reference herein, of various laser/detector/spectrometer systems for evaluating inelastic scattering include: U.S. Pat. No. 8,072,595 to inventors Bastiaans et al. (discussing use of a programmable delay generator triggered by firing of a laser including for elastic or inelastic scattering optical time domain detection; U.S. Pat. No. 2008/0198365 to inventors Treado, et al. (discussing why and how inelastic scattering and Raman spectra can be used to identify molecular species); and US 2010/0309464 to Treado et al. (discussing Raman chemical imaging using pulsed laser excitation and time-gated detection).

Regardless of the timing selection method used, it is common practice to use a separate, dedicated device, subsystem, or method to pre-determine the target range. The timings can then be calibrated based on the speed of light as well as any delays that are inherent to the system. Alternately, for some applications the distance to target can be fixed and all timings can be calibrated to that specific range.

In addition to controlling timing parameters of the system, an accurate distance measurement to the target is often desirable in order to focus the optical transmit and/or receive subsystems to optimize detection performance at that range, to optimize other controllable parameters such as data collection time, or to monitor or control other aspects of the system such as range interlocks.

There are several issues with the existing methodologies for determining range. A fixed range is generally only useful in a controlled laboratory setting as controlling the range precisely is generally not feasible in commercial settings. Using a separate range finder device or method also has several drawbacks. Range finders use a variety of methods to determine the range. Regardless of the methodology, the failure modes of the range finder are likely not the same failure modes as the standoff optical spectroscopy system, i.e. the range finder can fail in situations where, had the range been accurately determined, the spectroscopy would have succeeded in analyzing the target. Such situations may be different than situations in which the spectroscopy could not have succeeded at all. For instance, a very highly retro-reflective object can cause a LIDAR range finder to receive a signal much stronger than expected, saturating the receive electronics, but will not significantly impact the spectroscopy which is only weakly affected by the reflectivity.

Another issue is that by having a secondary range finder device the range finder either has to be bore sighted to the primary laser of the spectroscopy system, which adds additional complexity to the overall system, or the range finder will have a differing line of sight than the primary laser, adding uncertainty to the accuracy of the measurement. A secondary line of sight introduces the possibility that the range finder will strike a target that is not the actual target of interest and could potentially give the incorrect range to the target reducing the apparent reliability of the system.

Finally, a range finder will produce a range to the target that then must be converted into the correct gate timings ($T_{delay}$, $T_{gate}$) for the system. This introduces another possible source of error in that the calibration may either be done incorrectly or that there are delays inherent to the system that are not constant which again reduces the overall system accuracy or increases the system complexity.

Therefore, a need exists for a methodology of determining the gate timings required without using a supplementary device such as a range finder. This will reduce the complexity and increase the accuracy and reliability of such detection systems. As will be appreciated by the foregoing, the beneficial potential for such systems and techniques is tremendous. Yet the competing factors to make them accurate and practical make solutions elusive and unpredictable. This is evidenced by the many different attempts and approaches in the state the art. Working at relatively large distances, but at nano- and even pico-second time domains with substantial signal-to-noise, are imposing challenges.

2 SUMMARY OF THE INVENTION

It is therefore a principle object, feature, aspect or advantage of the invention to provide methods, apparatus, and systems which improve over or solve problems or deficiencies in the state of the art.

Other objects, features, aspects, or advantages of the invention include methods, apparatus, or systems which include one or more of the following.

It is an object of the invention to simplify the design and operation of a standoff Raman or other optical spectroscopy system by utilizing a distance measurement made using the Raman or other inelastic scattering spectroscopy measurements to control the setup and operation of the Raman or other optical measurement.

It is another object of the invention to improve the reliability and sensitivity of standoff Raman scattering or other inelastic scattering spectroscopy measurements by utilizing a distance measurement made by the Raman or other optical system to optimize controllable parameters of the standoff Raman or other optical spectroscopy system such as timings and focus distances.

Aspects of the present invention comprise a method for utilizing the inelastic optical scattering signal from a target and/or from the intermediate media between the sensor and the target to determine the optimal detection system settings to maximize the desired signal from the target, and/or minimize the background signals. A desirable feature is that by using the inelastic scattering signal of the intermediate media rather than the well-known method of using the elastic scattering (reflected light) from the target, the measurement is relatively insensitive to the reflectivity and orientation of the target. Another desirable feature is a reduction in the overall complexity of the system by reducing the need for an additional range finder device as a secondary component or by reducing the performance requirements for such an additional rangefinder. Another desirable feature is improvement of the performance and/or reliability of the detection system by determining the range by using the same components and methodology as the primary system.

Other aspects of the invention include implementing methodologies as summarized above into apparatus and systems.

These and other objects, features, aspects, and advantages of the invention will become more apparent with reference to the accompanying specification, drawings, and claims.

3 BRIEF DESCRIPTION OF THE DRAWINGS

The drawings, as summarized below, illustrate features and aspects of the invention or its background in conjunction with exemplary embodiments of the invention which follow thereafter.

FIG. 1A depicts a highly diagrammatic illustration of a typical system set up and, according to aspects of the present invention, three fundamental regions that the receiver can be gated to detect. FIG. 1A includes an illustration of the time-dependence of the signal due to inelastic emissions from the intermediate medium and from the target, assuming the target generates measurable inelastic scattering.

Figure 1A:
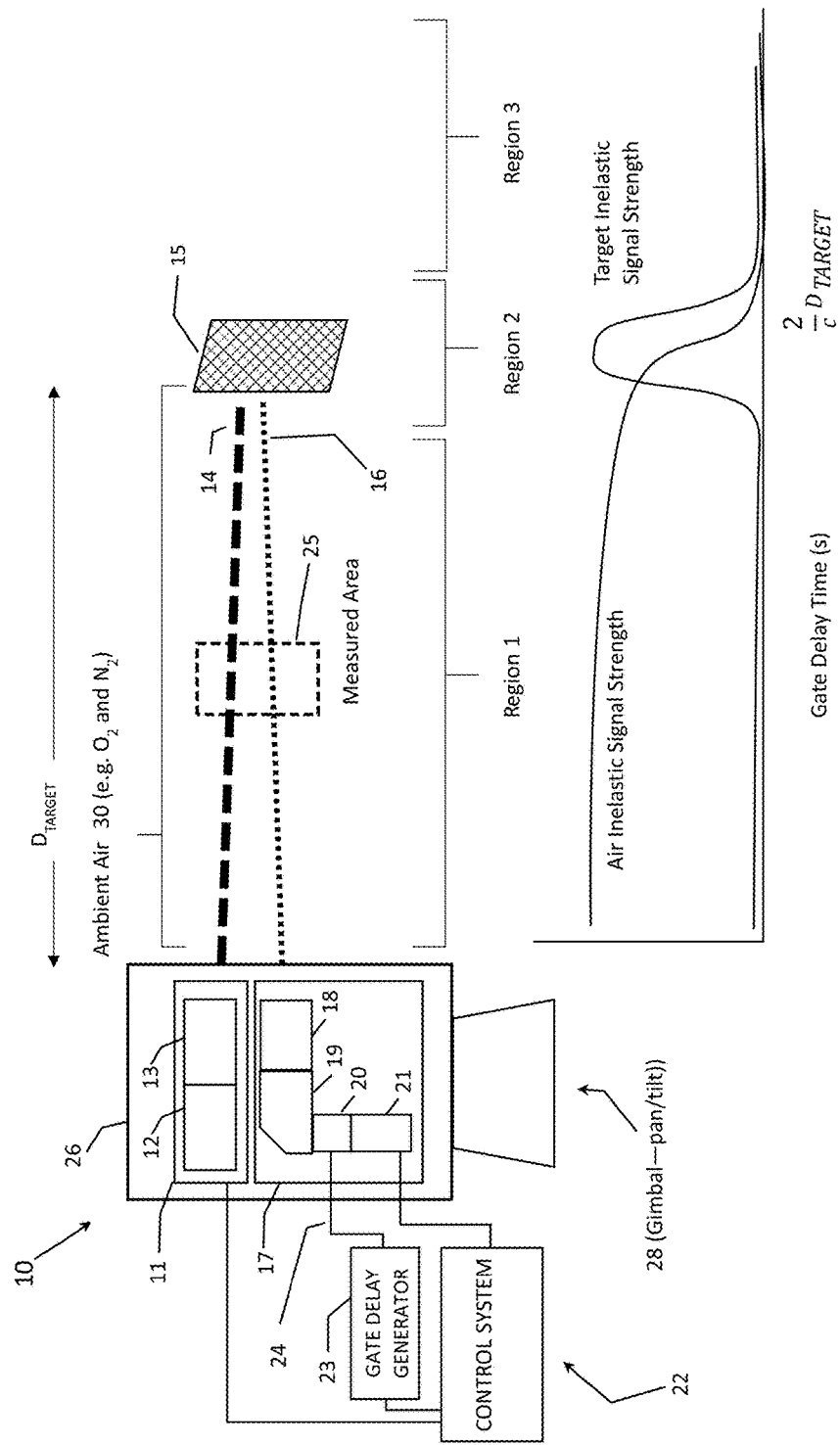
FIG. 1B is a flow chart of a methodology of estimating range to a target according to one exemplary embodiment of the invention.
FIG. 1C is a flow chart of a methodology of optimizing acquisition of inelastic scattering from a target for improved detection of chemical species of interest according to an exemplary embodiment of the invention.
FIG. 1D is a flow chart of a methodology of both estimating range to target and optimizing acquisition of inelastic scattering from it according to an exemplary embodiment of the invention.
Figure 6:
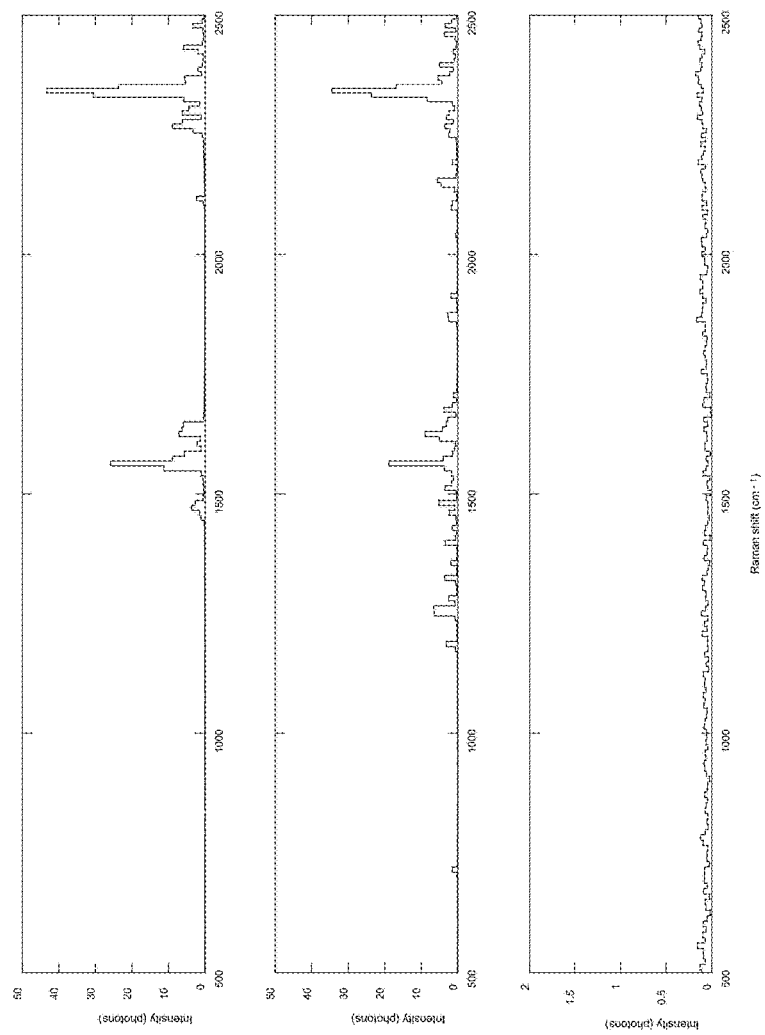

FIG. 6 shows measured data (intensity versus Raman shift) acquired using a deep-ultraviolet standoff Raman spectroscopy system at each of the three regions of FIG. 1A that can be used according to aspects and embodiments of the present invention relative a target which exhibits weaker inelastic scattering. In this case, even if the signal due to target is too weak to use, the target range may be determined by the suppression of the oxygen and nitrogen peaks.

Figure 7:
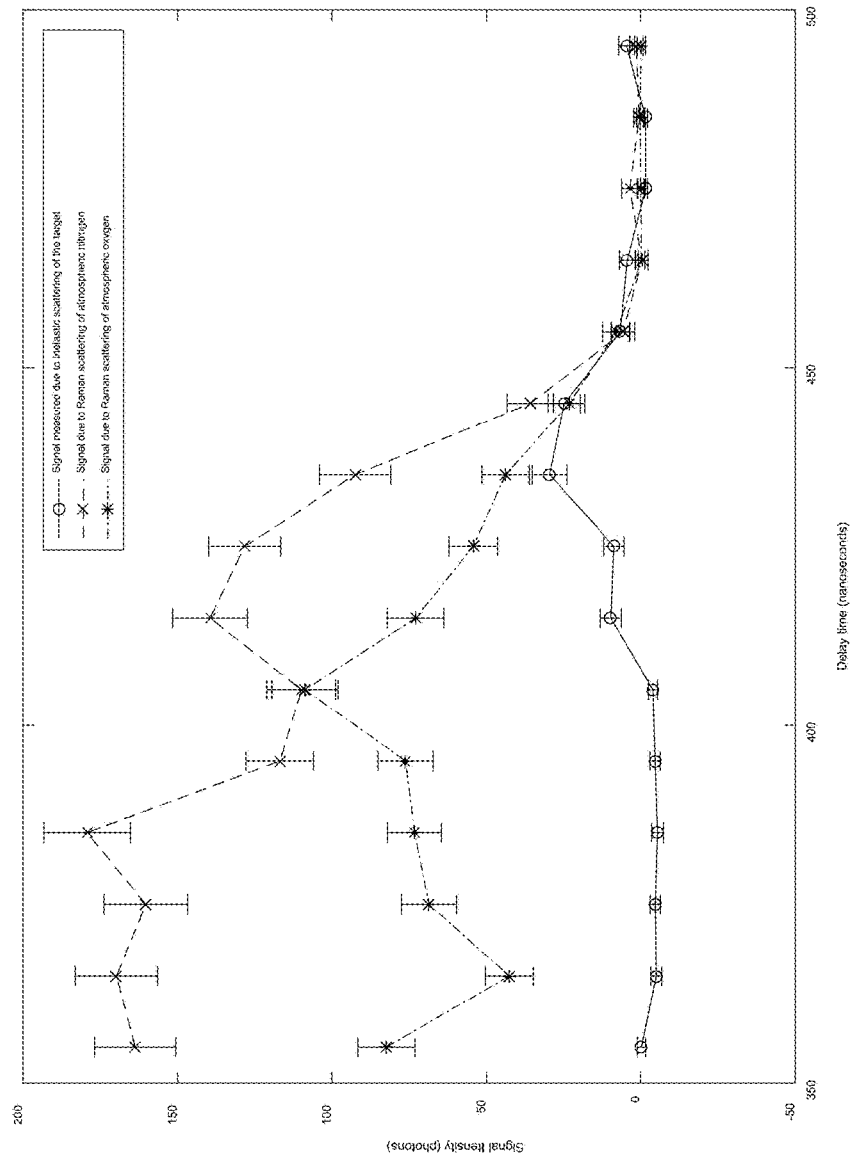

FIG. 7 shows processed data corresponding to the measurement setup of FIG. 6, showing processed data for gate delays at 10 nanosecond intervals.

FIG. 8 depicts a highly diagrammatic illustration of an alternate system set up according to aspects of the present invention. FIG. 8 includes an illustration of the time-dependence of the signal due to inelastic emissions from the intermediate medium and from the target, assuming the target generates measurable inelastic scattering.

4 DETAILED DESCRIPTION OF EXEMPLARY EMBODIMENTS ACCORDING TO THE INVENTION

4.1 Overview

For a better understanding of the invention, examples of forms it can take will now be described in detail. It is to be understood, however, that the following examples are neither exclusive nor inclusive of all forms and embodiments the invention can take. Variations obvious to those skilled in the art will be included within the invention, which is defined by the claims.

For instance, the descriptions below will mention certain pulsed UV lasers of indicated characteristics as a target-illuminating source, certain optical arrangements for both focusing the laser towards a target and collecting scattering from the target, certain gate generation techniques for differentiating portions of the collected scattering based on time-of-flight, certain spectrometry components and techniques, and certain spectrometry processing components and techniques; all in the context of aspects of the present invention. It is to be understood that these components and techniques can vary according to design and need, and be implemented with the aspects of the invention in analogous ways to those discussed below. For example, the exemplary embodiments focus upon Raman-type spectrometry. Aspects of the invention can be applied in analogous ways to other SOS techniques.

Additionally, certain spectral ranges and timing selections are discussed in the following examples. Those parameters can differ according to need or desire of the designer.

4.2 Generalized System

A central feature of the invention is intentionally look for and differentiate return inelastic scattering based on the following:

(1) Assume that inelastic scattering from intermediate molecules between the stand-off device and the target that otherwise could contribute to difficulty in extracting relevant inelastic scattering content from a target should, by itself, have a spectral content that differs from the inelastic scattering from the molecules of materials at the target. Rotational-vibrational spectroscopy can be used, which is a species of molecular spectroscopy related to infrared and Raman spectra of molecules in the gas phase. Transitions involving changes in both vibrational and rotational states are sometimes called rovibrational (or ro-vibrational) transitions. Aspects of the exemplary embodiments take advantage of ro-vibrational transitions for identifying gas-phase constituents of air (which is substantially $O_2$ and $N_2$), in its evaluation of return collected scattering from the target.

(2) Sweep through and evaluate each of a series of a plurality of small time-of-flight-controlled windows of collected scattering:
 (a) beginning at or shortly after initial firing of the illumination causing the scattering and assuming such content contains inelastic scattering from intermediate molecules and not target molecules; and
 (b) continuing at least until a time that exhibits inelastic scattering different from intermediate molecules and indicative of target molecules;

(3) using knowledge of time-of-flight for the differentiated collected scattering assumed to be from the target molecules to either:
 (a) estimate range to target;
 (b) optimize the best collected content for SOS evaluation to improve accuracy of identification of the target molecules; or
 (c) both.

In one alternative, the evaluation can continue after the time of content exhibiting inelastic scattering indicative of target molecules until a time where the collected content is indicative of beings spatially past the target or otherwise differentiable from inelastic scattering of target molecules. In another embodiment, instead of differentiating inelastic scattering of intermediate molecules and target molecules, the windows of collected inelastic scattering can just be evaluated for content indicative of target molecules, without evaluating content assumed to be before or after the target.

4.2.1 Apparatus

FIG. 1A depicts a simplified representative of a system 10 set for which embodiments of the invention could be applied, such as a system designed for standoff Raman detection of chemicals. A transmitter subsystem 11 containing a monochromatic pulsed light emitting source 12 such as a laser and beam conditioning optics 13, emits light 14 which then travels towards the target 15 which may inelastically scatter light 16 back at the receiver subsystem 17. In addition, while the source-emitted photons 14 are traveling towards the target, they may interact with intermediate molecules, such as $N_2$ and $O_2$ (see generally ref. no. 30), which may also scatter light back towards the receiver 17.

In one implementation, shown in FIG. 1A, the receiver subsystem 17 comprises beam collection optics 18, wavelength dispersive device 19 such as a spectrometer, optical gate 20, and detector 21. The optical gate 20 only allows photons that are received at a specific time or narrow range of times to pass through the gate 20 onto the detector 21 which can measure the spectrum of the inelastic scattered signal generated from a limited area (e.g. for one gate delay area 25 in FIG. 1A, which shifts for different gate delays), whose distance from the detection system is determined by the time delay between the laser pulse emission and the optical gate time. The optical gate 20 may be integrated with the detector 21 such as an intensifier tube, or may be separate such as a Kerr gate. The system 10 shown includes a control system 22 which can set the time delay from when the light pulse 14 is emitted to when the gate 20 is opened to any of a variety of delay times, so as to allow for photons scattered from varying ranges to be recorded. The time difference between the emitting of the light pulse 14 to the opening of the gate 20 will be herein referred to as the gate delay 24. A gate delay generator 23 associated with control system 22 is programmable to set the optical gate 20 width and its timings. At least transmitter 11 and receiver 17 can be integrated in a housing 26 which can be pan/tilt adjustable by, e.g., gimbal mount 28.

4.2.2 Operation

For a fixed, short duration gate width, increasing the gate delay 24 causes the area 25 that scattered light is collect from to be shifted away from the system 10. Referring to FIG. 1A, this area 25 passes through three distinct regions (assuming the transmitter 11 is pointing at a solid target of interest). Region 1 is the region completely in front of the target 15, during this region the return signal 16 will only be the signal from any intermediate molecules 30, such as $N_2$ or $O_2$ (air). In Region 2, the return signal 16 will be partially of intermediate molecules 30 and partially of the signal of the target 15 of interest itself. In this region the strength of the signal from air will decrease since the range of distances that correspond to the programmed gate delay 24 and width include distances behind the target 15. Depending on the composition of the target, there may or may not be inelastically scattered photons from the target which may affect the overall strength of the return signal. When the gate delay 24 is increased to a point where the area of collection is completely behind the target 15 (e.g. in Region 3), the photons from the light source 14 will be either completely or partially blocked. In either case it is possible to observe a new plateau of signal strength in this region that is distinct from the signal strength from the first region. If the light was completely blocked, there will be almost no signal from this region. Some signal may be recorded by the detector 21 in this case, but that signal is largely generated by noise sources, ambient light sources, and low-probability effects such as signal return from afterglow in the laser 12 or multiple-scattering events. These can be calculated and calibrated for based on a particular configuration of a system.

Because in this example you do not know the correct range yet, you sweep through an entire set of gate delays to figure it out. It is very helpful to see the signal drop to approximately zero, which tells you that you have finally swept the region 25 completely past the target.

In practice, we have found it beneficial to sweep through all 3 regions. This allows us to "bracket" the target distance using the region 1 and 3 data, which can be important as a confirmation that the system is operating as expected, and limit the distances to be analyzed to exactly measure the target range. The region 2 data is then analyzed to find the gate delay corresponding either to the maximum target signal (usually preferred if the target has a strong signal) or to the range at which the air signal falls to about half (works if the target does not generate signal).

A range measurement can be performed by sweeping the gate delay 24 through some or all of the three regions described. As the delay 24 is adjusted, the inelastically scattered signals may be recorded and analyzed to determine where each of the three regions are located as a function of gate delay without any a priori knowledge of where the target is actually located. The recorded signals may include wavelength information. The wavelength spectrum of inelastically scattered light from the intermediate media 30 is sufficiently different from the spectrum of inelastically scattered light from the target 15 to allow data processing to discriminate between the two signals as an aid in determining the range. See graph in FIG. 1A which is roughly aligned with Regions 1, 2 and 3 to illustrate how signals from these Regions can be differentiated.

See, for example, FIG. 1A. The detector is simultaneously measuring light intensity at a multiplicity of wavelengths due to the wavelength dispersive element 19. Note however an alternate implementation which does not use a wavelength dispersive element, but instead uses wavelength selective elements (color filters), in which case the recorded signal or signals (depending on how many detectors with wavelength filters are used) is a time-varying voltage or current.

The inelastic scattered spectrum of the target 15 may be taken as some processed subset of the data collected at various gate delays 24, such as a simple sum of the data collected at gate delays between the optimum gate delay minus the laser pulse duration and the optimum gate delay plus the laser pulse duration, or may be subsequently measured by fixing the gate timings based on this measurement and acquiring additional data. It is common practice with a standoff optical spectroscopy system to acquire spectral data of the target for as long of a duration as is reasonable (e.g. 10 to 60 seconds) to improve the accuracy and precision of the spectrum. In that case, a short period of time (e.g. 0.1 to 5 sec.) can be used for range measurement followed by a longer period (e.g. 5 to 55 sec.) with timings fixed for the optimum detection. These timings can be varied according to need or desire.

In the above example, the measurable spectrum includes the inelastic spectrum and elastically scattered light. The elastically scattered light corresponds to one extra peak in the measurable spectrum, at a location we know is the "elastic scattering peak". As is common practice, but not required, in this example the receiver 17 was designed so that the elastically scattered light does not even fall within the measuring range of detector.

Figure 3:
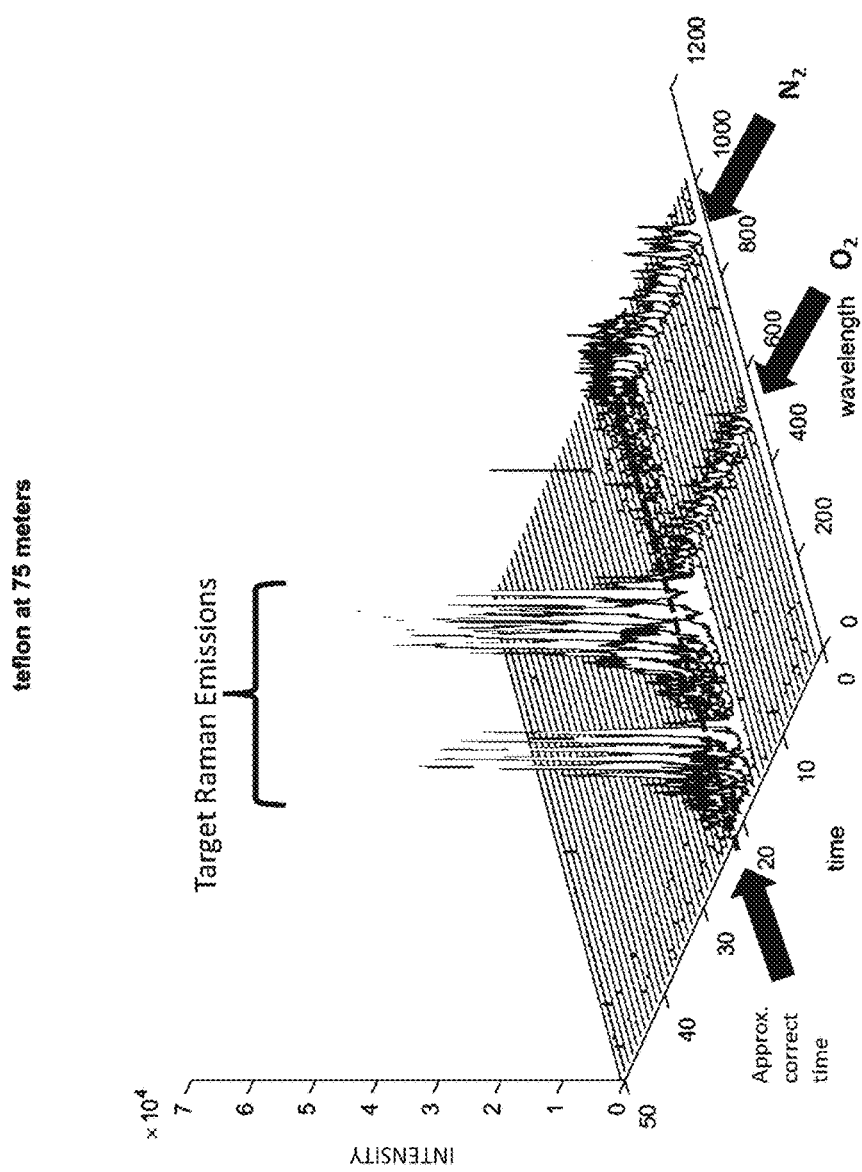
FIG. 3 shows another example of measured data (intensity versus both time of measurement and wavelength) acquired using a deep-ultraviolet standoff Raman spectroscopy system that can be used according to aspects and embodiments of the present invention relative a second target which exhibits stronger inelastic scattering.

Thus, the system can easily distinguish elastic from inelastic and ignore elastic, and/or be configured to not even have elastic in the signal being analyzed. In FIG. 3, the elastic scattering would show up as a peak at time=22, but the detector in this case is designed and positioned such that the elastically scattered light does not strike a sensitive area of the detector.

Another embodiment of the above, applicable when the target 15 is of such material and shape that it generates significant inelastic scattering, is the case where the system is constructed in a way in which the scattering from any intermediate molecules or particulates 30 is not detectable on that system, in which case there will only be return signal from target 15 of interest. In this case the above methodology can be modified from attempting to discern the differences and time domain location of the three regions (Regions 1, 2, and 3 of FIG. 1A) and instead simply look at where the inelastic scattering return signal 16 has the greatest strength.

In such a case, where for instance the intermediate molecules are air, the sensor cannot see the signal from air (as it is designed that way). But it is still possible to determine the target distance by using the signal at other inelastic scattering wavelengths. Imagine if you designed the detector in FIG. 3 so that it could only measure wavelengths from pixel 1 to pixel 400 (wavelengths 1-400), instead of 1 to 1000 (wavelengths 1-1000). The two diagonal ridges for $O_2$ and $N_2$ would not be on the detector. But you can still see that the right delay time (gate delay) as about 22 by looking at the big peaks labeled "Target Raman Emissions".

Another embodiment of the either of the above would be to walk the gate delay 24 and analyze the data in real time instead of taking a data set of the entire time sweep and performing a post-processing analysis. This would be accomplished by a very similar methodology where the gate delay 24 could start from closer than the closest expected target or further away than the farthest expected target based on the system's operating envelope. The analysis would then be performed in manner looking for a significant change in signal strength and declaring that region to be a target of interest in the case where the intermediate molecules are detectable by the system. In the case where the system cannot detect the intermediate particles, the routine would stop when the peak of the return from the target was reached.

An extension of any of the above methodologies could be applied to detect that case where the photons emitted from the light source 12 strike multiple targets at multiple different distances due to the emitted beam 14 partially impinging on a near target and partially impinging on a farther target or targets, or in the case where the target of interest is past a partially blocking object such as a fence or grate. In this case as the photon beam 14 travels past each obstacle or target this would be accompanied by a proportional degradation of signal from the intermediate molecules 30. Each region of degradation would then each correspond to multiple potential targets. These could then either be reported as multiple potential ranges for the system to use, or potentially for an operator to select, or if it is known a priori if a particular range, such as the furthest, was always desirable to be used, the system could be configured to return that particular range as the correct range to be used in properly timing the system.

Figure 1B:
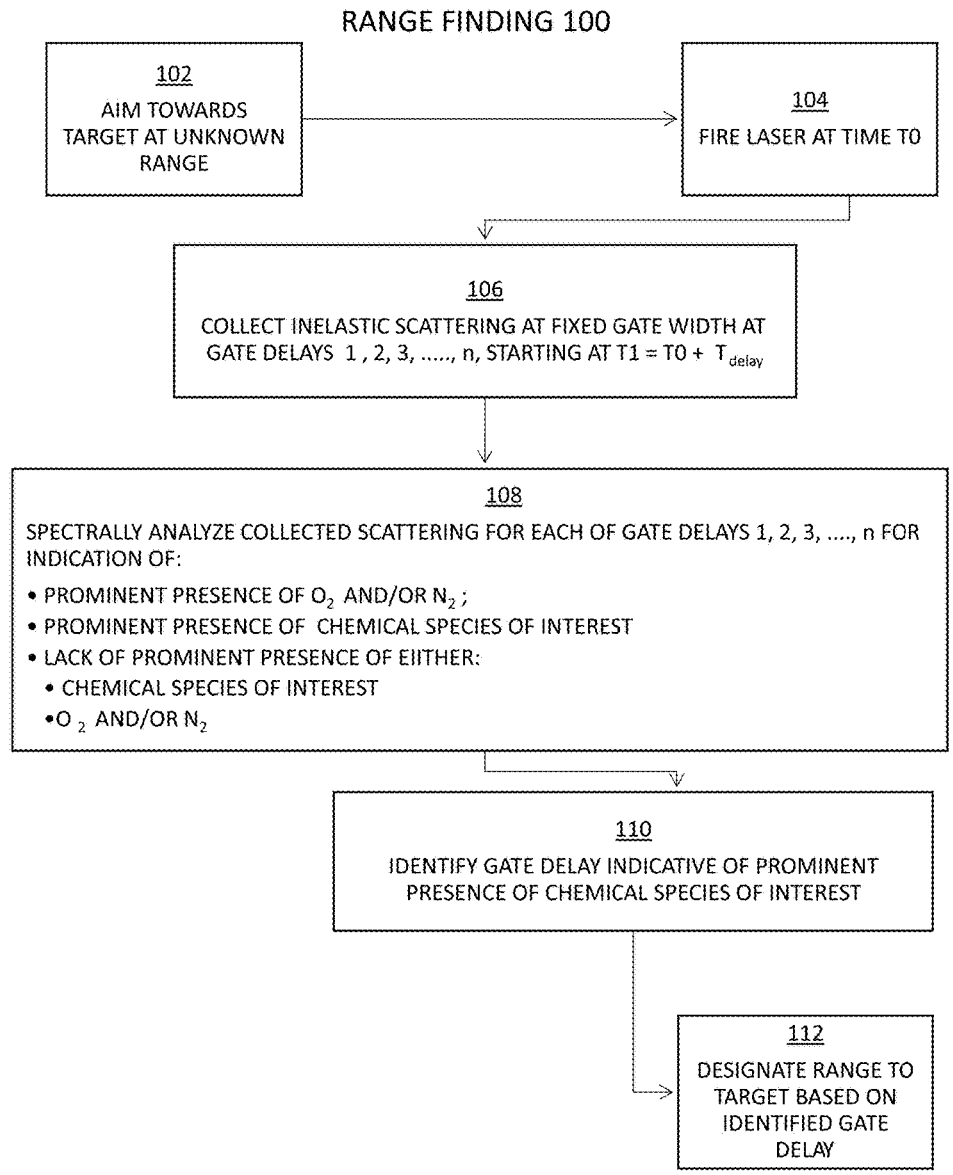
Figure 1C:
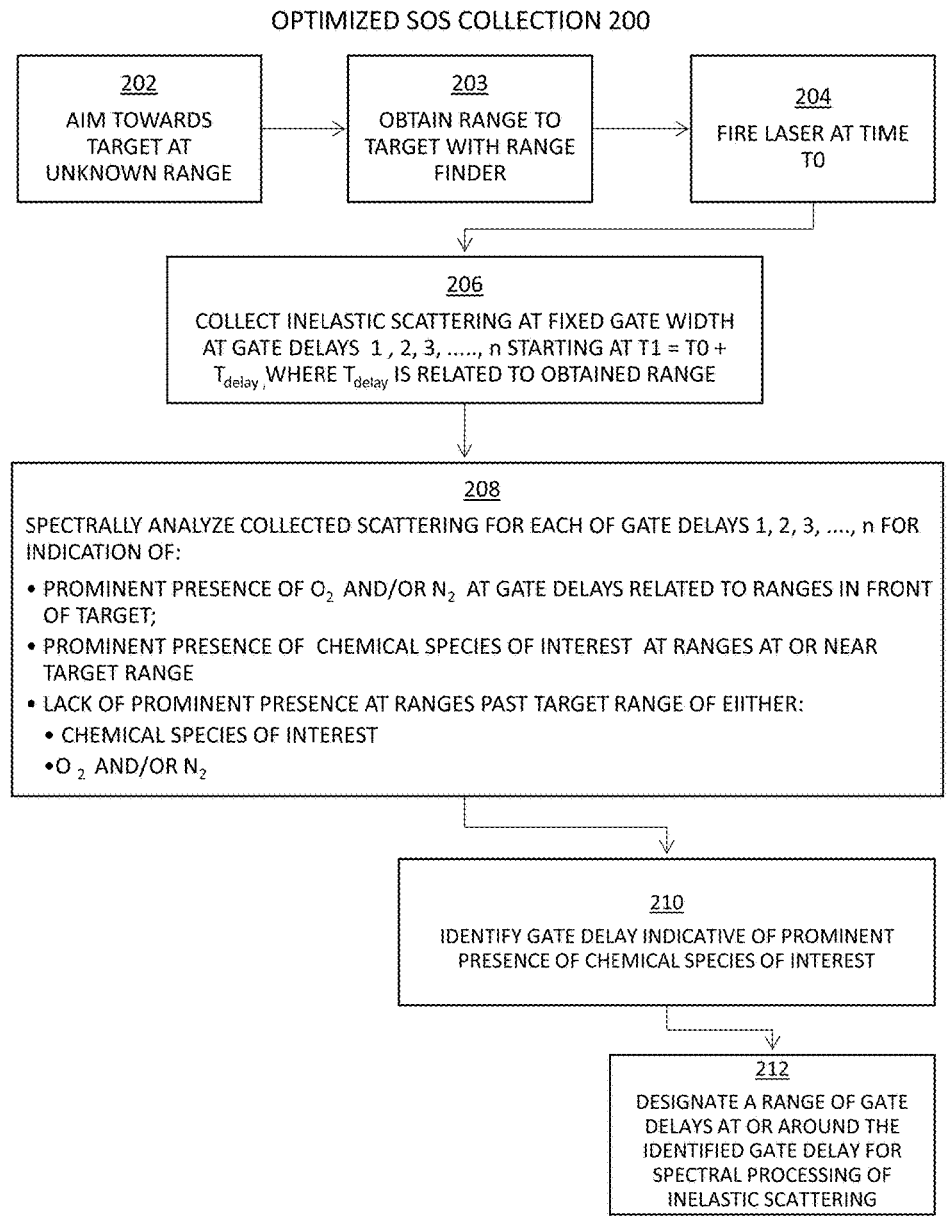
Figure 1D:
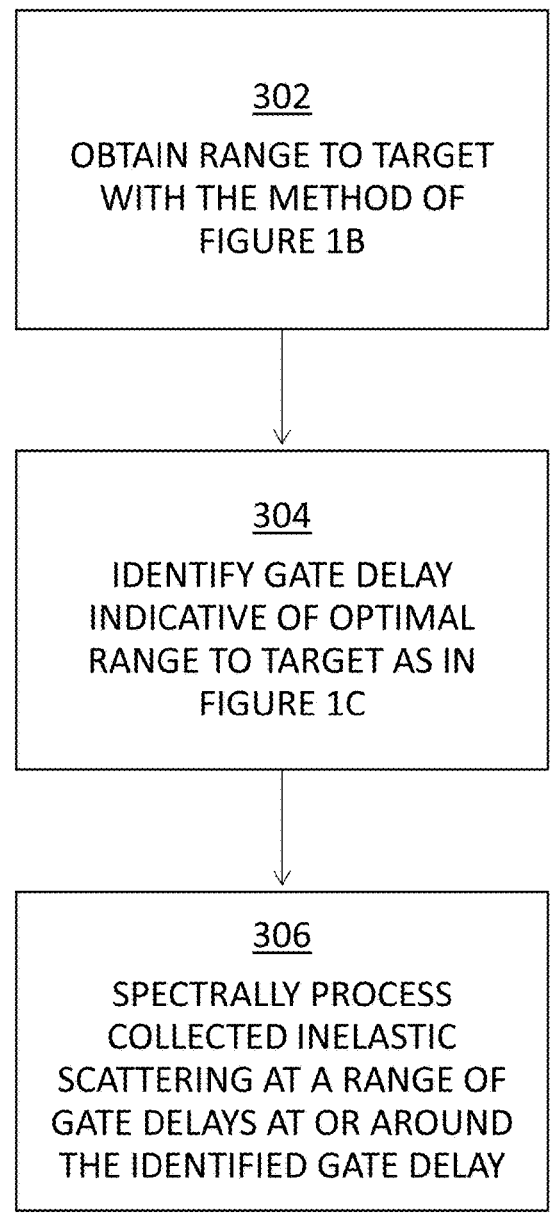

As will be appreciated from the foregoing, the general concept of evaluating the returned scattering based on timed gates or windows of scattering collection allow the system several potential benefits. FIGS. 1B-D are generalized flow charts illustrating several applications to stand-off distance SOS. As will be further appreciated by those skilled in the art, the ways in which these steps can be practiced can take advantage of the teachings in the patent literature incorporated by reference above. This would include selection of appropriate laser 12 (and its operation), detector 14 (and its operation), as well as the ability to generate highly controllable gate delays and gate widths for the collection of scattering at detector 14 and, then, selecting which gated windows to use for either range finding or spectral processing.

Range Finding Mode

FIG. 1B uses the techniques for a method 100 of range finding. This could replace conventional range finders as follows:

Step 102: The system 10 of FIG. 1A could be aimed at a target 16 of unknown range.

Step 104: Laser 12 is fired.

Step 106: Scattering is collected at detector 17 for a series of fixed gate widths starting at a time after first firing of laser 12 but likely to be from molecules between detector 17 and target 15, and continuing until likely from at target 15 and then, optionally, beyond target 15.

Step 108: Detector 17 and control system 22 spectrally analyze each collected gated window of scattering. By a priori knowledge of the spectral fingerprint of at least one of the main constituents of air (e.g. $O_2$, $N_2$, or $O_2$ and $N_2$), the spectral analysis will look for indications of those gated windows that prominently exhibit one or more constituents of air versus at least those where those constituents are diminished in favor of more prominence of spectral features indicative of species of interest. Optionally, the analysis can include looking for indications of those gated windows that prominently exhibit neither the constituents of air or the species of interest.

Step 110: If there is clear differentiation of the foregoing, the gate delay with indication of presence of a species of interest will be identified automatically (e.g. by its prominent intensity in a spectral range correlated to one or more species of interest), and will be assumed to indication scattering from the target.

Step 112: Knowing the offset between time T0 (when the laser 12 first fired or some other reference time) and the essentially speed-of-light return of scattering to detector, and having the ability to discern with sufficient precision and accuracy each of the series of gate delays (e.g. at nanoscale time frames), high resolution of range to target can be designated.

This technique meets one or more of the objects of the invention. It does not require a separate conventional range finder. It takes advantage of components that can also be used for other purposes. It can identify scattering very fast in temporal terms (almost real time) and with high spatial resolution. As will be further discussed, this can be at milli- or micro-scale time scale (including spectral processing with sufficiently capable digital processors) and at minute spatial scale (converting time in nano- or even pico-scale gatings into respective distances).

Improved SOS Detection Mode

FIG. 1C uses the techniques for a method 200 of collecting scattering for SOS purposes. By the technique (with range to target by a conventional rangefinder), high resolution of location of the target engenders better detection results.

Step 202: The system 10 of FIG. 1A could be aimed at a target 16 of unknown range.

Step 203: Range to target is estimated automatically by conventional rangefinder.

Step 204: Laser 12 is fired.

Step 206: Scattering is collected at detector 17 for a series of fixed gate widths starting at a time after first firing of laser 12 but likely to be from molecules between detector 17 and target 15, and continuing until likely from at target 15 and then, optionally, beyond target 15.

Step 208: Detector 17 and control system 22 spectrally analyze each collected gated window of scattering. By a priori knowledge of the spectral fingerprint of at least one of the main constituents of air (e.g. $O_2$, $N_2$, or $O_2$ and $N_2$), the spectral analysis will look for indications of those gated windows that prominently exhibit one or more constituents of air versus at least those where those constituents are diminished in favor of more prominence of spectral features indicative of species of interest. Optionally, the analysis can include looking for indications of those gated windows that prominently exhibit neither the continents of air or the species of interest.

Step 210: If there is clear differentiation of the foregoing, the gate delay with indication of presence of a species of interest will be identified automatically (e.g. by its prominent intensity in a spectral range correlated to one or more species of interest), and will be assumed to indication scattering from the target.

Step 212: Knowing the offset between time T0 (when the laser 12 first fired or some other reference time) and the essentially speed-of-light return of scattering to detector, and having the ability to discern with sufficient precision and accuracy each of the series of gate delays (e.g. at nanoscale time frames), high confidence of and resolution of distance to the target can be designated, and a range of gate delays at and around the identified gate delay can be selected from which to collect inelastic scattering and spectrally analyze it for indications (or not) of presence of chemical species of interest.

This technique meets one or more of the objects of the invention. It can identify scattering very fast in temporal terms (almost real time) and with high spatial resolution so that the richest scattering can be focused upon with the likelihood of better detection results. As will be further discussed, this can be at milli- or micro-scale time scale (including spectral processing with sufficiently capable digital processors) and at minute spatial scale (converting time in nano- or even pico-scale gatings into respective distances).

Range Finding and Optimized Detection Mode

FIG. 1D uses the techniques for a combined method 300 of both range finding and detection. This eliminates the need for a conventional range finder, but also can improve detection:

Step 302: The concepts of the method of FIG. 1B are used to determine range to the relevant part of a target 15 at unknown range.

Step 304: The concepts of the method of FIG. 1C are then used, informed by the range to target that has been obtained from Step 302, to focus in on the richest inelastic scattering from the target.

Step 306: The potential for high performance SOS is enabled by the quick and spatially accurate range finding, coupled with quick and accurate processing of optimized inelastic scattering from the target.

This technique meets one or more of the objects of the invention. It does not require a separate conventional range finder. It takes advantage of components that can also be used for SOS detection. It can identify scattering very fast in temporal terms (almost real time) and with high spatial resolution. As will be further discussed, this can be at milli- or micro-scale time scale (including spectral processing with sufficiently capable digital processors) and at minute spatial scale (converting time in nano- or even pico-scale gatings into respective distances). Even though range finding precedes SOS processing, the time scale and spatial resolution for both are at least acceptable for most applications, including hazardous or explosive material detection.

4.3 Specific Embodiment

A specific embodiment of the method utilizes a standoff deep ultraviolet Raman detection system. The system includes a 248 nm KrF excimer laser source operating at 500 pulses per second at a typical energy of between 1 and 4 mJ. The laser beam is transmitted towards a distant target at distances of tens of meters to hundreds of meters via a telescope which also collects returned light. The returned light is separated from the outbound laser light using a dichroic element. The laser beam is injected into the telescope as a slightly diverging beam, so that it is transmitted as a collimated or nearly collimated beam when the telescope focus is adjusted to optimize collection of received light from a selected target distance. The telescope is incorporated in a steerable gimbal (see non-limiting example of gimbal 28 in FIG. 1A) so that the beam can be steered towards a target.

As is well known to those skilled in this technical art, a dichroic is an optical element that selectively passes light of one range of wavelengths while reflecting light of another range of wavelengths, and is thus used in this example to separate a common outbound+return path outside the gimbal into two separate paths inside the gimbal—one for the outbound laser and one for the inbound inelastically-scattered light.

Optionally, additional wavelength selective filters provide a means of blocking light of wavelengths that are far outside the range of interest from reaching wavelength dispersive element. Although that light theoretically would not cause a problem due to the wavelength dispersive element directing it away from the detector, in practice it can cause nuisance noise due to low-probability reflections within the receive, i.e. "stray light". Alternate designs which do not require the dichroic and/or additional filters are possible and will be readily apparent to those skilled in this technical art.

Returned light, passing through the dichroic wavelength separator and additional wavelength selective filters, is collected onto a bundle of fiber optics which route the light to a wavelength dispersive spectrometer. The spectrometer disperses light at wavelengths from about 240 nm to about 270 nm onto a UV sensitive intensified CCD camera (ICCD). Electronics controlling the intensifier tube on the intensified CCD camera allow the intensifier to be gated on at selected times for periods of at least 0.3 nanoseconds. The ICCD can be gated at more than 500 gates per second. In this example, the intensifier cannot be operated at shorter gate widths for electrical reasons. The focal plane array of the CCD is configured to allow light to be integrated for integration times of 0.1 second, corresponding to 50 individual laser pulses and intensifier gates. A one-dimensional spectrum is read out of the ICCD into a computer memory every 0.1 second.

An optical sensor attached to the laser generates an electronic pulse with high timing precision when the laser fires. The sensor pulse is routed to a programmable electronic delay generator which generates an ICCD gate pulse of 30 nanoseconds width at a selected delay time. The optical sensor can be integrated at laser 12 in FIG. 1A or otherwise sense and report operation states of laser 12 to control system 22. Gate delay generator 23 could be integrated with, at, or associated with the gate 20 and/or detector 21 of FIG. 1A and be controlled via control system 22. References such as the Treado references, supra, give details about gate delay generation and gate control, as well as referencing the same based on laser operational state or timing.

The sensor system includes video cameras to enable the operator to accurately point the gimbal at a desired target, and a built-in infrared rangefinder which may be used to provide an initial estimate of the range to the target, but is not required.

When the operator initiates a Raman chemical analysis of the selected target, the infrared rangefinder is read by the control system. If the built-in infrared rangefinder is not used or is not able to provide an estimated range to the target, the control system uses pre-calculated formulas and look-up tables to select positions for motors which control telescope focusing to adjust optical focusing of the telescope to achieve acceptable signal coupling for the outbound laser and return signal from Raman interactions over many ranges, for instance by adjusting focus to approximately the correct focus for an infinite range. The delay generator (e.g. gate delay generator 23 of FIG. 1A is programmed to initially gate (e.g. gate 20 of FIG. 1A) the ICCD (e.g. a part of detector 21) at a time corresponding to the optimal gate delay for a target range corresponding approximately to the closest target range at which the preset telescope focus provides acceptable signal coupling. Every 0.1 second, a spectrum is read out of the ICCD, the ICCD is cleared, and the ICCD gate delay is increased by a fixed 100 nanoseconds. Data collection at increasing delay times continues while the stored spectra are analyzed.

Analysis of the time-dependence of Raman signal strength due to air allows identification of gate delays, and therefore ranges, corresponding to Region 1 and Region 3 of FIG. 1A, by the presence and/or absence of Raman signal from air. This provides a means to bracket the target range without requiring that any of the measurements occur at a gate delay corresponding to the actual target range. The analysis includes provision for the possibility that the first selected gate delay was already too long. This situation is identifiable by absence of Raman signal from air in the first (smallest gate delay) measurement. In that case, the measurement is stopped, the telescope focus is adjusted to achieve acceptable signal coupling at closer ranges, and the process is repeated, possibly up to several times, until at least one measurement is identified as corresponding to Region 1 of FIG. 1A, and at least one measurement is identified as corresponding to Region 3 of FIG. 1A. These two measurements bracket the actual target range. An estimated range is taken as the closer of the two ranges.

The estimated range from this process, or an estimated range taken from the infrared rangefinder, is used by the control system along with pre-calculated formulas and look-up tables to select positions for motors which control telescope focusing to adjust optical focusing of the telescope to achieve near-optimal signal coupling for the outbound laser and return signal from Raman interactions at that range. The estimated range is also used to program the delay time of the ICCD gate pulse, including the round-trip time for the laser to and from the target and a constant offset to account for the inherent delays in the electronics.

The delay generator (e.g. gate delay generator 23 of FIG. 1A) is programmed to initially gate (e.g. gate 20 of FIG. 1A) the ICCD (e.g. a part of detector 21) at a time corresponding to the optimal gate delay for a target range equal to the estimated range to the target minus 30 nanoseconds, so that initially, light is gated onto the focal plane of the ICCD for ranges that are closer than the estimated range to the target. Every 0.1 second, a spectrum is read out of the ICCD, the ICCD is cleared, and the ICCD gate delay is increased by a fixed 10 nanoseconds. Data collection at increasing delay times continues while the stored spectra are analyzed.

Analysis of the time-dependence of Raman signal strength due to air and due to non-air materials allows detection of the optimal gate delay corresponding the actual target distance. The analysis includes provision for the possibility that the first selected gate delay was already too long, which can happen if the infrared rangefinder reported an estimated range to the target which was at least a few meters longer than the actual range. This situation is identifiable by absence of Raman signal from air in any of the measurements. In that case, the gate delay times are changed to search towards decreasing delays.

When sufficient data are available to calculate the optimal gate delay, the gate delay is programmed to that value and the ICCD is cleared in preparation for acquiring a Raman spectrum from the target. Other settings such as intensifier gain, integration time, camera readout settings, and laser power can be changed. If the measured optimal gate delay is sufficiently close to the original estimated optimal gate delay, the optical focus of the system need not be adjusted. A Raman analysis of the target is performed. Data acquired during the range-finding process may or may not be included in the data used to analyze the target chemistry.

4.4 Proof of Concept

Principals upon which aspects of the invention are based are set forth below, with specific reference to the mentioned figures.

Figure 2:
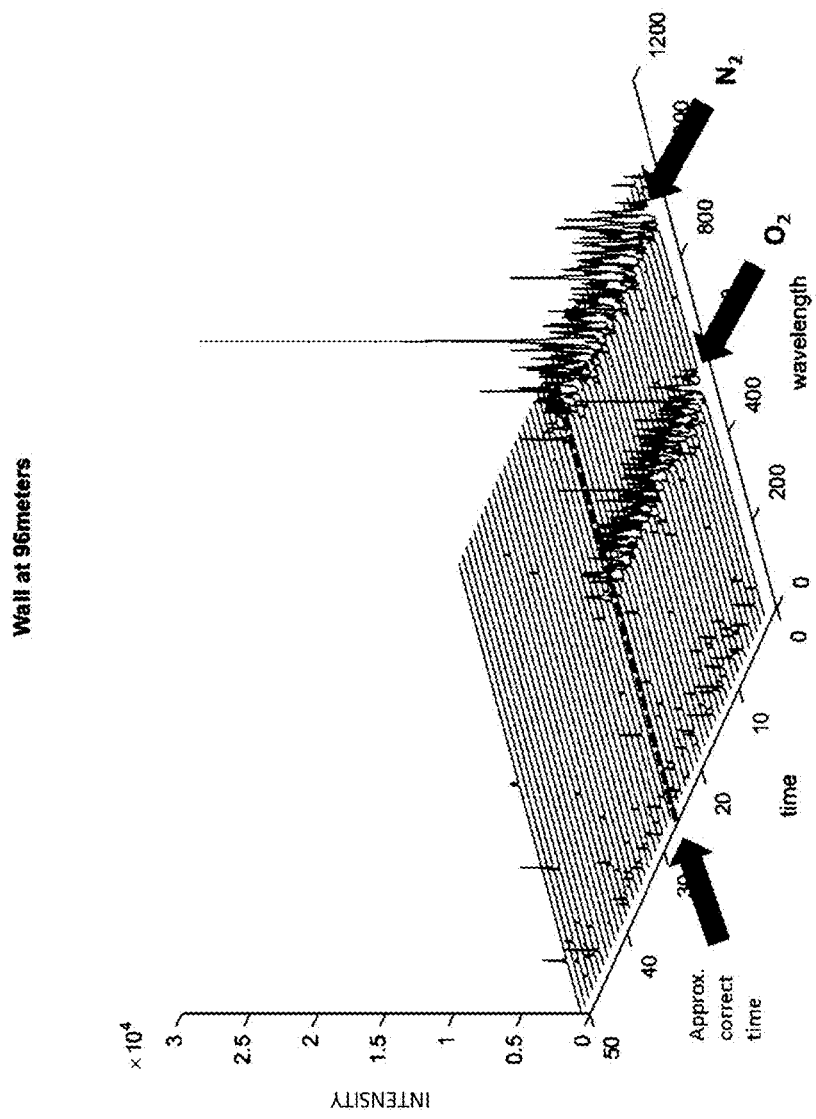
FIG. 2 shows an example of measured data (intensity versus both time of measurement and wavelength) acquired using a deep-ultraviolet standoff Raman spectroscopy system that can be used according to aspects and embodiments of the present invention relative a first target which has weak inelastic scattering.

FIG. 2 shows measured data acquired using a deep-ultraviolet standoff Raman spectroscopy system. The transmitter and receiver (e.g. 11 and 17 of FIG. 1A) are integrated into a single system (e.g. housing 26). The system (e.g. system 10 of FIG. 1A) is aimed at a wall 96 meters away, comprised of material with a very weak inelastic scattering signal. Spectra were collected at various gate time delays, with the gate width fixed at 30 nanoseconds in each case. Each spectrum was collected for a fixed data collection duration of 100 milliseconds using a pulsed laser source operating at 500 pulses per second and a pulse width of approximately 10 nanoseconds. Spectra at gate delay settings less than about the $25^{th}$ gate delay setting include clear spectral signals from Raman scattering from oxygen (labelled $O_2$ near channel 500 in the wavelength axis) and nitrogen (labelled $N_2$ near channel 900 in the wavelength axis.) These signals are clearly missing for longer gate delays. It is clear that the approximately correct gate delay to select light from the target is the delay corresponding to the $26^{th}$ measurement in the series.

FIG. 3 shows measured data acquired using a deep-ultraviolet standoff Raman spectroscopy system. The transmitter and receiver (e.g. 11 and 17 of FIG. 1A) are integrated into a single system (e.g. system 10). The system is aimed at a piece of Teflon™ 75 meters away. Spectra were collected at various gate time delays, with the gate width fixed at 30 nanoseconds in each case. Each spectrum was collected for a fixed data collection duration of 100 milliseconds using a pulsed laser source operating at 500 pulses per second and a pulse width of approximately 10 nanoseconds. Spectra at gate delay settings less than about the $20^{th}$ gate delay setting include clear spectral signals from Raman scattering from oxygen (labelled $O_2$ near channel 500 in the wavelength axis) and nitrogen (labelled $N_2$ near channel 900 in the wavelength axis.) These signals are clearly missing for longer gate delays. Spectra at gate settings from about the $18^{th}$ to about the $22^{nd}$ delay include strong spectral features from Raman scattering from Teflon, which are present at all wavelengths but most prominent at wavelengths near channel 100 and 400. It is clear that the approximately correct gate delay to select light from the target is the delay corresponding to about the $20^{th}$ measurement in the series.

Figure 4:
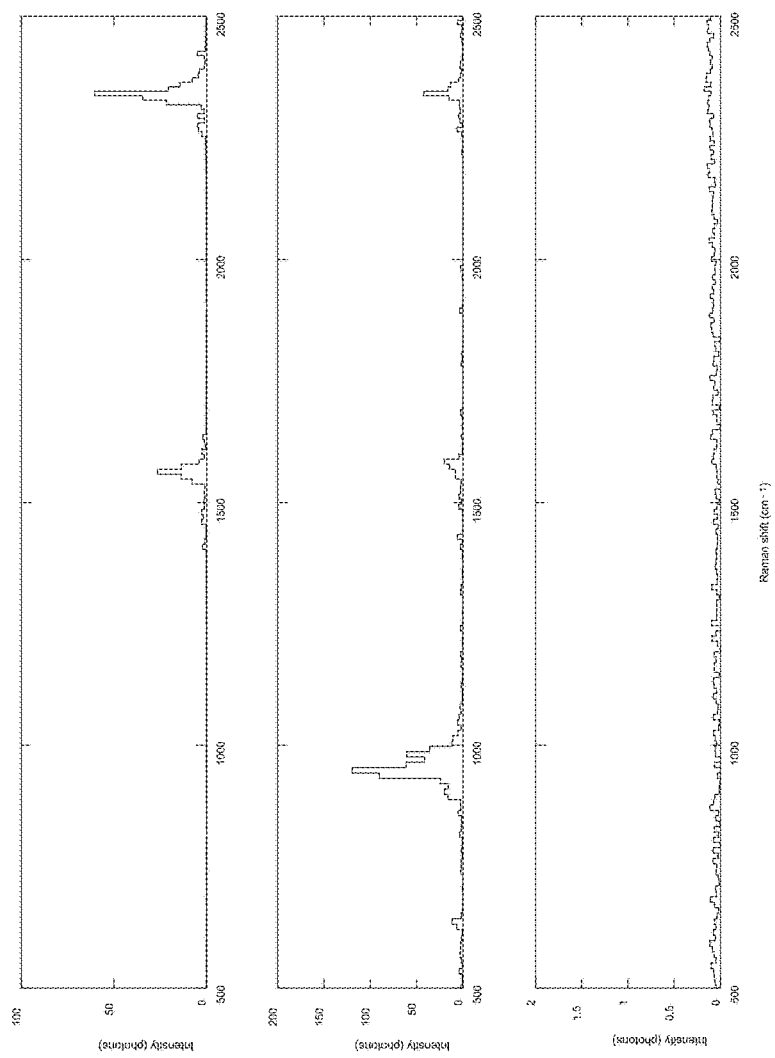
FIG. 4 shows measured data (intensity versus Raman shift) acquired using a deep-ultraviolet standoff Raman spectroscopy system at each of the three regions of FIG. 1A that can be used according to aspects and embodiments of the present invention relative a target which exhibits stronger inelastic scattering.

FIG. 4 shows measured data acquired using a deep-ultraviolet standoff Raman spectroscopy system. The laser and detector are integrated into a single system (e.g. system 10 of FIG. 1A). The system is aimed at a target which has strong Raman emission spectra at a range of approximately 67 meters. TOP: Spectrum measured at a delay time of approximately 400 nanoseconds. MIDDLE: Spectrum measured at a delay time of approximately 440 nanoseconds. BOTTOM: Spectrum measured at a delay tome of approximately 480 nanoseconds. Note vertical scale changes.

The spectra were collected for a fixed data collection duration of 100 milliseconds each using a pulsed laser source operating at 500 pulses per second and a pulse width of approximately 10 nanoseconds. The spectra are measured using a wavelength-dispersive spectrometer (e.g. spectrometer 19 of FIG. 1A) coupled to an intensified CCD detector array (e.g. gate 20 and detector 21 of FIG. 1A). The spectra were time-gated by turning on the intensifier tube high voltage for 30 nanoseconds at various time delays after the laser emission.

Spectral peaks near 1553 $cm^{-1}$ and 2330 $cm^{-1}$ due to air are strong in the first measurements, weaker in the 2nd measurement, and not present in the 3rd measurement. This means the correct delay time for the target range is between 400 and 480 nanoseconds. A large spectral peak near 950 $cm^{-1}$ is visible at 440 nanoseconds, but not 400 or 480 nanoseconds. This means the correct delay time for detecting the source of the 950 $cm^{-1}$ signal is approximately 440 nanoseconds.

Figure 5:
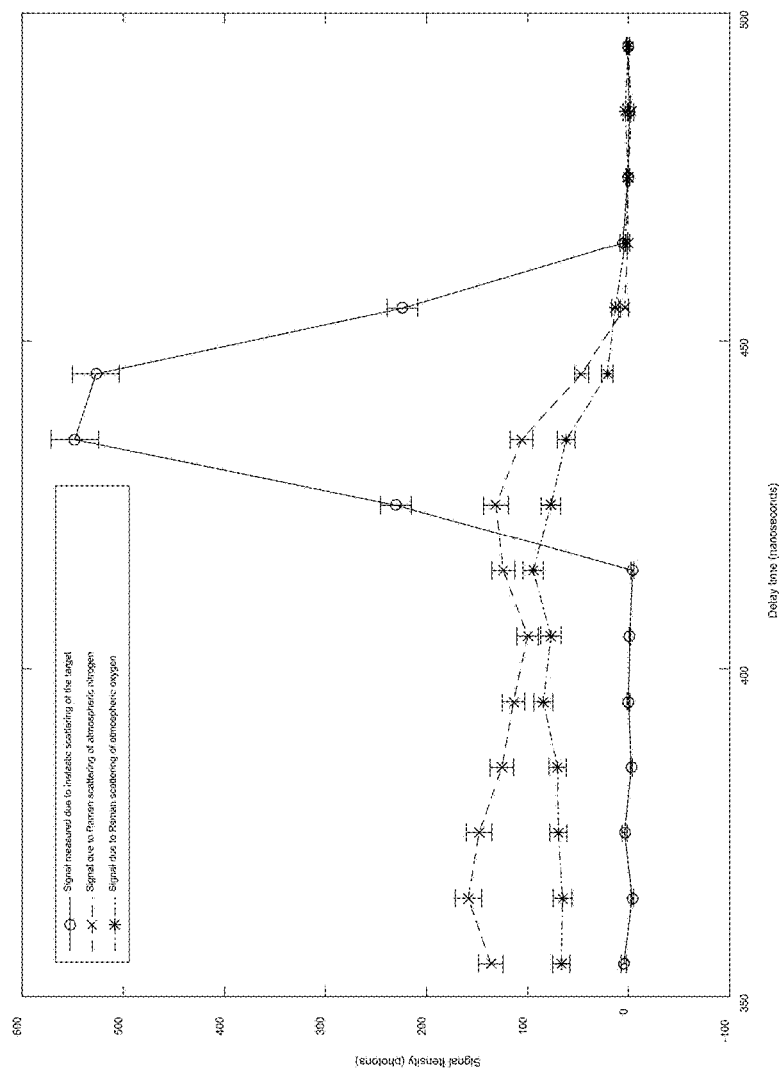
FIG. 5 shows processed data corresponding to the measurement setup of FIG. 4, showing processed data for gate delays at 10 nanosecond intervals.

FIG. 5 shows processed data corresponding to the measurement setup of FIG. 4, showing processed data for gate delays at 10 nanosecond intervals. For each spectral measurement, the signal due to Raman scattering of the target was measured as the sum of the spectrum over wavelength ranges corresponding to Raman shifts of 800 $cm^{-1}$ to 1355 $cm^{-1}$ and 1755-2130 $cm^{-1}$. The signal due to Raman scattering of atmospheric oxygen was measured as the sum of the spectrum over the wavelength range corresponding to Raman shifts of 1485 cm$^{-1}$ to 1625 cm$^{-1}$ minus the sum of the spectrum over ranges corresponding to 1355 to 1425 and 1685 to 1755 cm$^{-1}$. The signal due to Raman scattering of atmospheric nitrogen was measured as the sum of the spectrum over the wavelength range corresponding to Raman shifts of 2260 cm$^{-1}$ to 2400 cm$^{-1}$ minus the sum of the spectrum over ranges corresponding to 2130 to 2200 and 2460 to 2530 cm$^{-1}$.

The optimal delay time to acquire a Raman spectrum of the target is approximately 440 nanoseconds. The peak in the Raman spectrum from the target at delay times of 425 to 455 nanoseconds is sufficient to accurately determine the optimal delay time to a reasonable accuracy and precision.

FIG. 6 shows measured data acquired using a deep-ultraviolet standoff Raman spectroscopy system. The laser and detector are integrated into a single system (e.g. system 10 of FIG. 1A). The system is aimed at a target which has weak Raman emission spectra at a range of approximately 67 meters. TOP: Spectrum measured at a delay time of approximately 400 nanoseconds. MIDDLE: Spectrum measured at a delay time of approximately 440 nanoseconds. BOTTOM: Spectrum measured at a delay tome of approximately 480 nanoseconds. Note vertical scale changes.

The spectra were collected for a fixed data collection duration of 100 milliseconds each using a pulsed laser source operating at 500 pulses per second and a pulse width of approximately 10 nanoseconds. The spectra are measured using a wavelength-dispersive spectrometer coupled to an intensified CCD detector array. The spectra were time-gated by turning on the intensifier tube high voltage for 30 nanoseconds at various time delays after the laser emission.

Spectral peaks near 1553 cm$^{-1}$ and 2330 cm$^{-1}$ due to air are strong in the first measurements, weaker in the 2nd measurement, and not present in the 3rd measurement. This means the correct delay time for the target range is between 400 and 480 nanoseconds. For this target, there are no strong Raman features, but weak emissions in the ranges 1100-1500 cm$^{-1}$ and 1600-2300 cm$^{-1}$ are visible in the middle spectrum.

FIG. 7 shows processed data corresponding to the measurement setup of FIG. 6, showing processed data for gate delays at 10 nanosecond intervals. For each spectral measurement, the signal due to Raman scattering of the target was measured as the sum of the spectrum over wavelength ranges corresponding to Raman shifts of 800 cm$^{-1}$ to 1355 cm$^{-1}$ and 1755-2130 cm$^{-1}$. The signal due to Raman scattering of atmospheric oxygen was measured as the sum of the spectrum over the wavelength range corresponding to Raman shifts of 1485 cm$^{-1}$ to 1625 cm$^{-1}$ minus the sum of the spectrum over ranges corresponding to 1355 to 1425 and 1685 to 1755 cm$^{-1}$. The signal due to Raman scattering of atmospheric nitrogen was measured as the sum of the spectrum over the wavelength range corresponding to Raman shifts of 2260 cm$^{-1}$ to 2400 cm$^{-1}$ minus the sum of the spectrum over ranges corresponding to 2130 to 2200 and 2460 to 2530 cm$^{-1}$.

The optimal delay time to acquire a Raman spectrum of the target is approximately 440 nanoseconds. The peak in the Raman spectrum from the target at delay times of 425 to 455 nanoseconds is sufficient to accurately determine the optimal delay time to a reasonable accuracy and precision.

The optimal delay time to acquire a Raman spectrum of the target is approximately 440 nanoseconds. The falloff in the Raman spectra from oxygen and nitrogen at delay times from 400 to 450 nanoseconds is sufficient to accurately determine the optimal delay time to a reasonable accuracy and precision.

4.5 Options and Alternatives

As mentioned above, the invention can take many forms and embodiments. Variations obvious to those skilled in this technical field are included within the invention, which is described by the appended claims. A few examples follow:

1. System Integration

The components to practice the above-described embodiments can vary. The examples above indicate a portable, field-robust, integrated apparatus that could include in a ruggedized housing 26 (FIG. 1A) not only laser and detector, but could also include the entire control system 22, delay generator 23, and ancillary components (e.g. wiring, circuits, electrical power source (e.g. battery), optics, etc. The gimbal mount 28 can take many forms and configurations. Non-limiting examples are tripod-based, vehicle mounted, or other. But variations are, of course, possible according to need or desire.

2. Optical Sub-System, Housing, and Aiming

The optics for operation of the embodiments can take many forms and configurations. Those skilled in the art will be familiar with the same. Non-limiting examples are given in the incorporated-by-reference citations supra.

3. Types of Targets and Chemicals of Interest, and Contexts of System Versus Targets (Moving, Non-Moving, Etc.)

Non-limiting examples are given in the incorporated-by-reference citations supra. It will be appreciated that one important application can be targets that could involve explosives such as IEDs, land mines, and the like. Hazardous/toxic materials are another non-limiting but important example. However, the invention is not limited thereto.

4. Illumination/Excitation Source

A pulsed UV laser is mentioned above. As will be appreciated, however, aspects of the invention can be applied in the context of other sources in analogous ways. Non-limiting examples are given in the incorporated-by-reference citations supra.

5. Detector Sub-System

Similarly, those skilled in the art are familiar with a variety of ways to not only generate and aim an illumination source, but also optically collect and then SOS process that collected energy. Non-limiting examples are given in the incorporated-by-reference citations supra.

One alternate embodiment 10' would replace the receiver system 17 and gate delay generator 23 of FIG. 1A with alternate hardware, shown in FIG. 8. In this embodiment, the receiver system 417 comprises an optical filter 418 and a detector 419 such as a photomultiplier tube, avalanche photodiode, CMOS or CCD detector, or a multiplicity of parallel optical filters and detectors. In this embodiment, the detector 419 need not be gated to receive signal with a gate delay corresponding to the range of a measured area. Instead, a continuous signal from the detector 419 proportional to the intensity of light received with wavelength within the range passed by optical filter 418 would be processed using a signal processing circuit 423. In one embodiment, the optical filter 418 limits the detector to receiving light only within a wavelength range corresponding to inelastic scattering of $O_2$ and/or $N_2$. FIG. 8 is for an alternate embodiment in which the data is collected not as a series of separate discrete spectral measurements at separate discrete gate delays, but rather is collected as one or more continuous signals over time, such as you would see as an o-scope trace. The illustrative graph of signal versus delay time in FIG. 8 is what you would see as signal coming out of the detectors 429.

In another embodiment incorporating in a unit 420 a multiplicity of filters 428 and detectors 429 (similar to 418 and 419), the receive signal is split into spectral bands using one or more dichroic filters 421 B, C, D, etc. The dichroic filters 421 B, C, D, etc. and optical filters 428 may be selected to pass light from multiple wavelength ranges such as the inelastic scattering peak of $O_2$ near 1553 $cm^{-1}$, the inelastic scattering peak of $N_2$ near 2330 $cm^{-1}$, inelastic scattering from about 200 $cm^{-1}$ to about 1400 $cm^{-1}$, inelastic scattering from about 2600 $cm^{-1}$ to about 4000 $cm^{-1}$ and/or the elastic scattering peak. The signal processing circuit 423 comprises amplifiers, frequency filters, and either digitizer or peak-detector circuit for each of the detectors. The design and operation of such signal processing circuits is well understood by skilled practitioners. One possible signal processing circuit for a detector/filter combination designed to sense inelastic scattering from the target in the range from about 200 $cm^{-1}$ to about 1400 $cm^{-1}$ is the signal processing circuit used in standard LIDAR systems such as that taught by Chien (U.S. Pat. No. 6,466,307 B2). Many others have been published. For range detection using the inelastic scattering from $O_2$, $N_2$, or both, or other chemical component of the medium between the sensor and target, the signal processing circuit would include a high-pass frequency filter element, similar in function to a nuclear pulse shaping amplifier (Knoll 1989: "Radiation Detection and Measurement," 2nd Ed. by Glenn F. Knoll (J. Wiley, NY, 1989), Chapter 16, Section III, "Pulse Shaping" pp. 564-582), incorporated by reference herein. In another embodiment, the signal processing circuit comprises amplifiers, digitizers, and digital signal processing.

6. Control Sub-System

Those skilled in the art are familiar with a variety of ways and components to provide programable control functions for the system as well as data processing functions. Such things as digital processors of a variety of types, forms, processing capabilities, and the like are available commercially. The designer would select the same based on need or desire. Non-limiting examples are given in the incorporated-by-reference citations supra.

7. Gating and Gating Control

The functions of the gating and its gate delay generator can be implemented in a variety of ways. Non-limiting examples are given in the incorporated-by-reference citations supra.

8. Utilizations a. Range finding

As indicated above, in one form, aspects of the invention could be used for range finding. It is to be understood that in the mode, it could replace other types of range finders. As mentioned, one example would be where range finding based on reflection from a target is not reliable or possible. The range finding according to the invention might also be used in combination with other range finders or techniques for cross-checking purposes. There may be uses that do not involve more than the range finding; in other words, that so not process the evaluated gated collected scattering spectrally or otherwise except to produce a range estimation to target.

b. Detection

Similarly, aspects of the invention can be employed without using the range finding.

c. Both

Importantly, as indicated above, both range finding and SOS detection according to aspects of the invention can both be used with certain benefits.

What is claimed is:

1. A method for optimizing the operation of a standoff inelastic scattering optical spectroscopy chemical analysis system to maximize detection of scattered light from a target a distance away from the analysis system comprising:
   a. utilizing time-dependence of an inelastic scattered light signal from the target and/or surrounding medium to:
      1. select a range of times at which to collect scattered light and/or
      2. focus optical elements and/or
      3. adjust mechanical or electrical settings to optimize detection performance at the target distance;
   b. wherein the analysis system comprises:
      1. a Raman spectroscopy system incorporating at least a pulsed laser source,
      2. an optical transmitter subsystem to direct light from the pulsed laser source towards the target,
      3. an optical receiver subsystem to collect scattered light from the target,
      4. a wavelength-dispersive component to separate received light based on wavelength,
      5. a time-sensitive subsystem which passes received light to a detector only during selected periods of time, in which the time-selective subsystem comprises an intensifier tube with controllable time delay and time width pulsed high voltage and the detector comprises a CCD or CMOS array;
      6. a multielement detector which generates an optical spectrum measurement proportional to spectral intensity of light falling on the detector during a period of time,
      7. a control subsystem which adjusts the focus of optical elements and/or varies the delay in timing of the time-selective subsystem over a multiplicity of delay times, and
      8. a signal processing system which stores and analyzes the measured spectra for each of the multiplicity of delay times to determine an optimal delay time to maximize detected Raman signal from the target.

2. The method of claim 1 in which the pulsed laser source comprises a pulsed laser operating with a pulse width of between 1 and 20 nanoseconds and a pulse repetition rate of between 1 and 10,000 pulses per second, and the controllable time delay of the intensifier tube comprise high voltage on/off times set with an accuracy and precision of 10 nanoseconds or less.

3. A method for optimizing the operation of a standoff inelastic scattering optical spectroscopy chemical analysis system to maximize detection of scattered light from a target a distance away from the analysis system comprising:
   a. utilizing time-dependence of an inelastic scattered light signal from the target and/or surrounding medium to:
      1. select a range of times at which to collect scattered light and/or
      2. focus optical elements and/or
      3. adjust mechanical or electrical settings to optimize detection performance the target distance;
   b. wherein the analysis system comprises:
      1. a Raman spectroscopy system incorporating at least a pulsed laser source,
      2. an optical transmitter subsystem to direct light from the pulsed laser source towards the target,
      3. an optical receiver subsystem to collect scattered light from the target,
      4. a wavelength-dispersive component to separate received light based on wavelength, 5. a time-selective subsystem which passes received light to a detector only during selected periods of time;
6. a multielement detector which generates an optical spectrum measurement proportional to spectral intensity of light falling on the detector during a period of time,
7. a control subsystem which adjusts the focus of optical elements and/or varies the delay in timing of the time-selective subsystem over a multiplicity of delay times, in which the control subsystem comprises an optical detector which detects the emission of the laser pulse and a programmable delay generator, each with a timing accuracy and precision of 10 nanoseconds or less, and
8. a signal processing system which stores and analyzes the measured spectra for each of the multiplicity of delay times to determine an optimal delay time to maximize detected Raman signal from the target.

4. A method for optimizing the operation of a standoff inelastic scattering optical spectroscopy chemical analysis system to maximize detection of scattered light from a target a distance away from the analysis system comprising:
 a. utilizing time-dependence of an inelastic scattered light signal from the target and/or surrounding medium to:
  1. select a range of times at which to collect scattered light and/or
  2. focus optical elements and/or
  3. adjust mechanical or electrical settings to optimize detection performance at the target distance;
 b. wherein the analysis system comprises:
  1. a Raman spectroscopy system incorporating at least a pulsed laser source,
  2. an optical transmitter subsystem to direct light from the pulsed laser source towards the target,
  3. an optical receiver subsystem to collect scattered light from the target,
  4. a wavelength-dispersive component to separate received light based wavelength,
  5. a time-selective subsystem which passes received light to a detector only during selected periods time;
  6. a multielement detector which generates an optical spectrum measurement proportional to spectral intensity of light falling on the detector during a period of time,
  7. a control subsystem which adjusts the focus of optical elements and/or varies the delay in timing of the time-selective subsystem over a multiplicity of delay times, in which the control subsystem comprises an electronic circuit which detects an electrical signal generated by the laser which is generated at a time before or after the emission of the laser at a known time relative to the emission of the laser with no more than 10 nanoseconds imprecision, and a programmable delay generator, and
  8. a signal processing system which stores and analyzes the measured spectra for each of the multiplicity of delay times to determine an optimal delay time to maximize detected Raman signal from the target.

5. The method of claim 4 wherein the electronic circuit which detects an electrical signal generated by the laser comprises a Q-switch gate.

6. A method for optimizing the operation of a standoff inelastic scattering optical spectroscopy chemical analysis system to maximize detection of scattered light from a target a distance away from the analysis system comprising:
 a. utilizing time-dependence of an inelastic scattered light signal from the target and/or surrounding medium to:
  1. select a range of times at which to collect scattered light and/or
  2. focus optical elements and/or
  3. adjust mechanical or electrical settings to optimize detection performance at the target distance;
 b. wherein the analysis system comprises:
  1. a Raman spectroscopy system incorporating at least a pulsed laser source,
  2. an optical transmitter subsystem to direct light from the pulsed laser source towards the target,
  3. an optical receiver subsystem to collect scattered light from the target,
  4. a wavelength-dispersive component to separate received light based on wavelength,
  5. a time-selective subsystem which passes received light to a detector only during selected periods of time;
  6. a multielement detector which generates an optical spectrum measurement proportional to spectral intensity of light falling on the detector during a period of time,
  7. a control subsystem which adjusts the focus of optical elements and/or varies the delay in timing of the time-selective subsystem over a multiplicity of delay, and
  8. a signal processing system which stores and analyzes the measured spectra for each of the multiplicity of delay times to determine at optimal delay time to maximize detected Raman signal from the target, in which the optimal delay time is determined based on the detecting a decrease in the intensity of the spectral features of oxygen at a Raman shift in the range 1503-1603 $cm^{-1}$ or nitrogen at a Raman shift in the range 2280-2380 $cm^{-1}$ as the delay time is increased from a delay time corresponding to distances closer than the target to a delay time corresponding to distances farther than the target.

7. The method of claim 6, in which the analysis system includes a means of measuring, receiving, or selecting a distance to target.

8. The method of claim 7, in which the determined optimal delay time is used to validate, verify, or adjust the distance to target as provided by the means.

9. The method of claim 6, in which the control system incorporates a means in the process of determination of delay times to measure distance to target.

10. A method for optimizing the operation of a standoff inelastic scattering optical spectroscopy chemical analysis system to maximize detection of scattered light from a target a distance away from the analysis system comprising:
 a. utilizing time-dependence of an inelastic scattered light signal from the target and/or surrounding medium to:
  1. select a range of times at which to collect scattered light and/or
  2. focus optical elements and/or
  3. adjust mechanical or electrical settings to optimize detection performance at the target distance;
 b. wherein the analysis system comprises:
  1. a Raman spectroscopy system incorporating at least a pulsed laser source,
  2. an optical transmitter subsystem to direct light from the pulsed laser source towards the target,
  3. an optical receiver subsystem to collect scattered light from the target, 4. a wavelength-dispersive component to separate received light based on wavelength,
  5. a time-selective subsystem which passes received light to a detector only during selected periods of time;
  6. a multielement detector which generates an optical spectrum measurement proportional to spectral intensity of light falling on the detector during a period of time,
  7. a control subsystem which adjusts the focus of optical elements and/or varies the delay in timing of the time-selective subsystem over a multiplicity of delay, and
  8. a signal processing system which stores and analyzes the measured spectra for each of the multiplicity of delay times to determine an optimal delay time to maximize detected Raman signal from the target, in which the optimal delay time is determined based on detecting an increase and then a decrease in the intensity of spectral features not attributable to components of air as the delay time is increased from a delay time corresponding to distances closer than the target to a delay time corresponding to distances farther than the target.

11. The method of claim 10, in which the analysis system includes a means of measuring, receiving, or selecting a distance to target.

12. The method of claim 10, in which the control system incorporates a means in the process of determination of delay times to measure distance to target.

13. A method for optimizing the operation of a standoff inelastic scattering optical spectroscopy chemical analysis system to maximize detection of scattered light from a target a distance away from the analysis system comprising:
  a. utilizing time-dependence of an inelastic scattered light signal from the target and/or surrounding medium to:
    1. select a range of times at which to collect scattered light and/or
    2. focus optical elements and/or
    3. adjust mechanical or electrical settings to optimize detection performance at the target distance;
  b. wherein the analysis system compromises:
    1. a Raman spectroscopy system incorporating at least a pulsed laser source,
    2. an optical transmitter subsystem to direct light from the pulsed laser source towards the target,
    3. an optical receiver subsystem to collect scattered light from the target,
    4. a wavelength-dispersive component to separate received light based on wavelength,
    5. a time-selective subsystem which passes received light to a detector only during selected periods of time;
    6. a multielement detector which generates an optical spectrum measurement proportional to spectral intensity of light falling on the detector during a period of time,
    7. a control subsystem which adjusts the focus of optical elements and/or varies the delay in timing of the time-selective subsystem over a multiplicity of delay and
    8. a signal processing system which stores and analyzes the measured spectra for each of the multiplicity of delay times to determine an optimal delay time to maximize detected Raman signal from the target, in which the optimal delay time is determined based on a combination of factors including detecting a decrease in the intensity of spectral features attributable to oxygen and/or nitrogen and/or an increase and then a decrease in the intensity of spectral features not attributable to components of air as the delay time is increased from a delay time corresponding to distances closer than the target to a delay time corresponding to distances farther than the target.

* * * * *

UNITED STATES PATENT AND TRADEMARK OFFICE
CERTIFICATE OF CORRECTION

PATENT NO. : 10,352,863 B1  
APPLICATION NO. : 15/820039  
DATED : July 16, 2019  
INVENTOR(S) : Kenneth R. Pohl and Christopher Neglia It is certified that error appears in the above-identified patent and that said Letters Patent is hereby corrected as shown below:

In the Claims

In Column 20, Claim 3, Line 58:
INSERT --at-- after the word "performance"

In Column 21, Claim 4, Line 40:
INSERT --on-- after the word "based"

In Column 24, Claim 13, Line 4:
DELETE "compromises" after the word "system"
INSERT --comprises-- after the word "system"

Signed and Sealed this
Seventeenth Day of September, 2019

Andrei Iancu
*Director of the United States Patent and Trademark Office*